United States Patent
Auger et al.

(10) Patent No.: US 7,329,260 B2
(45) Date of Patent: Feb. 12, 2008

(54) KIT, GUIDE AND METHOD FOR LOCATING DISTAL FEMORAL RESECTION PLANE

(75) Inventors: Daniel D. Auger, Fort Wayne, IN (US); Mary J. Stewart, Leeds (GB); Gary S. Fenton, Huddersfield (GB); Steven G. Ingleson-Mace, Kent (GB); David P. Thomas, West Yorkshire (GB); Frederic Turquier, York (GB)

(73) Assignee: DePuy Products, Inc., Warsaw, IN (US)

( * ) Notice: Subject to any disclaimer, the term of this patent is extended or adjusted under 35 U.S.C. 154(b) by 445 days.

(21) Appl. No.: 10/609,171

(22) Filed: Jun. 27, 2003
(Under 37 CFR 1.47)

(65) Prior Publication Data

US 2006/0089653 A1 Apr. 27, 2006

Related U.S. Application Data

(60) Provisional application No. 60/392,717, filed on Jun. 28, 2002.

(51) Int. Cl.
*A61B 17/58* (2006.01)
(52) U.S. Cl. ....................................... 606/88
(58) Field of Classification Search ............... 606/79, 606/87–89
See application file for complete search history.

(56) References Cited

U.S. PATENT DOCUMENTS

| | | | |
|---|---|---|---|
| 4,566,448 A | | 1/1986 | Rohr, Jr. |
| 4,703,751 A | * | 11/1987 | Pohl ........................ 606/62 |
| 4,736,737 A | * | 4/1988 | Fargie et al. ............. 606/88 |
| 5,213,112 A | | 5/1993 | Niwa et al. |
| 5,314,482 A | | 5/1994 | Goodfellow et al. |
| 5,431,653 A | | 7/1995 | Callaway |
| 5,540,696 A | | 7/1996 | Booth, Jr. et al. |
| 5,630,820 A | | 5/1997 | Todd |
| 5,649,929 A | | 7/1997 | Callaway |
| 5,662,656 A | * | 9/1997 | White ..................... 606/88 |
| 5,676,668 A | * | 10/1997 | McCue et al. ........... 606/87 |

(Continued)

OTHER PUBLICATIONS

Keblish, Peter A., "Surgical Techniques in the Performance of Unicompartmental Arthroplasties", Operative Techniques in Orthopaedics, 1998, pp. 134-145, vol.8, No. 3, W.B. Saunders Company, USA.

(Continued)

*Primary Examiner*—Eduardo C. Robert
*Assistant Examiner*—Mary Hoffman

(57) ABSTRACT

A combination cutting and spacer guide has a cutting block portion and a guide arm portion. The cutting block portion has a cutting guide slot and holes to receive pins or drills for mounting the combination cutting and spacer guide to the femur. The cutting guide portion also has a cutting guide slot defining the distal femoral resection plane. The guide arm portion has a planar femoral and tibial surfaces and an elongate slot between the surfaces. A shim has a shim arm with contact surfaces for contacting part of the guide arm and part of one of the bones of the knee and a mounting member connected to the shim arm. The shim arm mounting member is receivable in the elongate slot of the guide arm to mount the shim to the guide arm to adjust the level of the femoral resection plane.

15 Claims, 10 Drawing Sheets

U.S. PATENT DOCUMENTS

| | | | |
|---|---|---|---|
| 5,720,752 A | * | 2/1998 | Elliott et al. .................. 606/88 |
| 5,735,904 A | | 4/1998 | Pappas |
| 5,782,925 A | | 7/1998 | Collazo |
| 6,290,704 B1 | * | 9/2001 | Burkinshaw et al. ......... 606/88 |
| 6,296,646 B1 | | 10/2001 | Williamson |
| 6,468,280 B1 | | 10/2002 | Saenger et al. |

OTHER PUBLICATIONS

Insall, John N., M.D., Surgery of the Knee, 1984, pp. 626-629, Churchill Livingston, USA.

P.F.C. Sigma Uni-Compartmental Knee System, Alternative Unicompartmental Surgical Technique, 1998, DePuy Orthopaedics, Inc., USA.

LCS UNI Surgical Technique, Unicompartmental Knee System with Porocoal Porous Coating. 0601-00-000 1988, DePuy Orthopaedics, Inc., USA.

LCS UNI Surgical Technique, Unicompartmental Knee System with Porocoal Porous Coating. 0601-00-000 (Rev. 1) 1988, DePuy Orthopaedics, Inc., USA.

LCS UNI Unicompartmental Knee System, Product Rationale, 0601-02-000, 1998, DePuy Orthopaedics, USA.

Minimally Invasive Solutions brochure pp. 8-9, no date available.

DePuy Orthopaedics Redacted Drawing No. 099846, no date available.

DePuy Orthopaedics Redacted Drawing No. 099811, no date available.

DePuy Orthopaedics Redacted Drawing No. 099810, no date available.

DePuy Orthopaedics Redacted Drawing No. 099812, no date available.

* cited by examiner

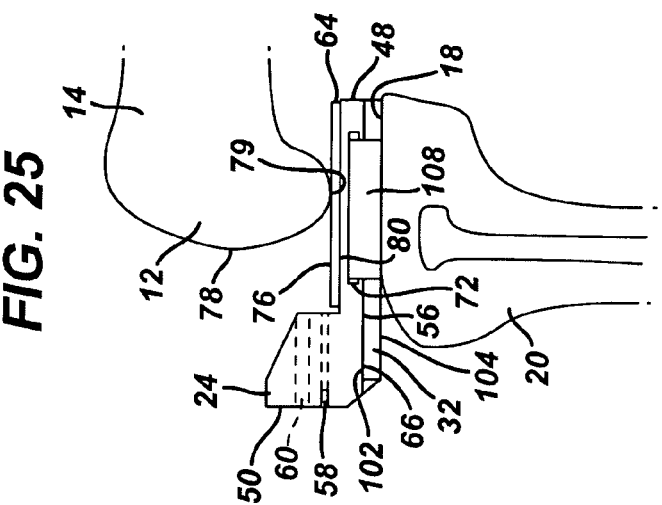
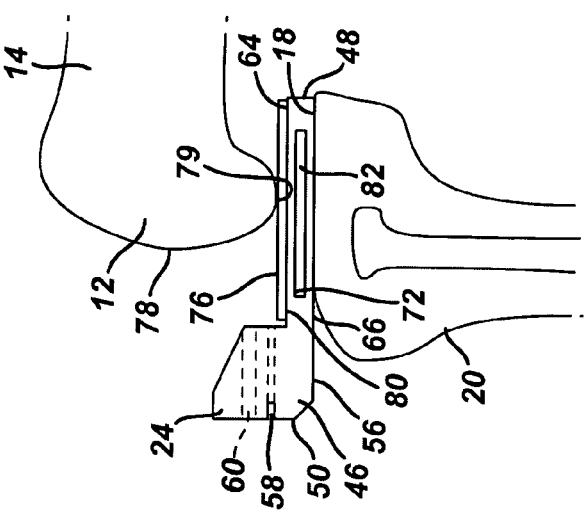
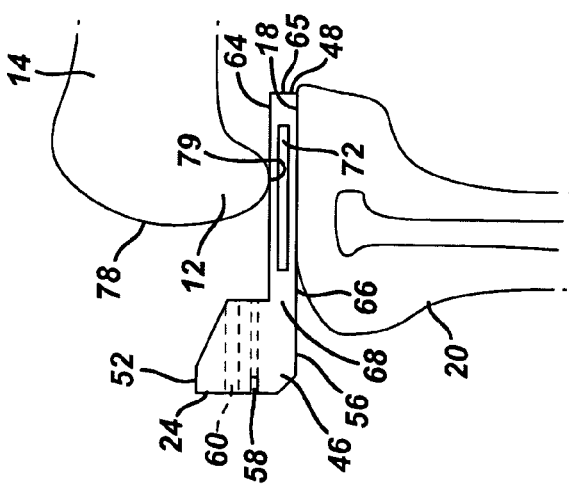

KIT, GUIDE AND METHOD FOR LOCATING DISTAL FEMORAL RESECTION PLANE

CROSS-REFERENCE TO RELATED APPLICATION

This application claims the priority benefit of U.S. provisional application No. 60/392,717, filed Jun. 28, 2002, entitled "Kit, Guide and Method for Locating Distal Femur Resection Plane," the disclosure of which is incorporated herein by reference, in its entirety.

BACKGROUND OF THE INVENTION

1. Field of the Invention

This invention relates to a kit, combination cutting and spacer guide, and method for use in determining the location of a plane for resecting a surface of a single condyle of the distal femur in a knee joint, relative to a reference surface on the proximal tibia, to prepare the femur for implantation of the femoral component of a unicompartmental knee joint prosthesis.

2. Description of the Prior Art

Accurate resection of a patient's bones is crucially important for success in an operation to implant a joint prosthesis. Accurate resection depends on accurate location of the resection planes. The orientations of the resection planes relative to the anatomical axis must also be accurately controlled to ensure proper alignment of the articulating surfaces of the joint after surgery, throughout the full range of joint motion. Proper location of the resection planes is important in achieving proper soft tissue balancing. Moreover, accurate location of the resection planes is necessary to minimize the amount of bone that is removed, while being sure to remove all bone tissue that is defective.

For implantation of a knee prosthesis, the location of the resection plane for the tibia is determined first, and the location of the femoral resection plane is then determined with reference to the tibial resection plane, generally after resection of the tibia. Accurate location of the tibial resection plane in a knee joint is commonly established using an alignment guide which includes an alignment rod which can be fastened to the tibia distally, close to the ankle. The rod extends along the tibia, parallel to the axis of the tibia. The tibial resection plane can then be defined relative to the tibial axis using a cutting block which can be attached to the alignment guide or to the proximal tibia. The tibial resection may then be performed along the tibial resection plane.

The distal femoral resection is performed along the distal femoral resection plane. The location of the distal femoral resection plane relative to the tibial resection plane will depend on factors which include the dimensions of the implant components that are to be used. Appropriate alignment and spacing of the femoral and tibial components should be maintained throughout the range of motion of the knee joint. This requires accurate location of distal, anterior and posterior femoral resection planes on the femoral component. In addition to the dimensions of the implant component, alignment and spacing can be affected by features of the patient's anatomy. For example, the alignment of the femoral resection planes can be arranged to provide a correction for varus and valgus deformations. It can also be required to ensure that the implanted femoral component is aligned with the natural condyle, to facilitate optimum coverage of femoral tissue and that the extent of overhang of the component beyond the femoral tissue is minimized.

When preparing a knee for a unicompartmental knee prosthesis, the relative positions of the tibial and femoral resection planes are significant for an additional reason: to ensure that the implant does not cause damage to the healthy side of the knee. Considering, for example, a unicompartmental knee prosthesis that is implanted on the medial side of a patient's knee, if too little bone is removed from the distal surface of the medial condyle, the native lateral condyle may be forced toward the tibial plateau, causing increased stress on the lateral meniscus and lateral side of the tibial plateau. Considering a unicompartmental knee prosthesis that is implanted on the lateral side of the patient's knee, if too little bone is removed from the distal surface of the lateral condyle, the native medial condyle may be forced toward the medial tibial plateau, causing increased stress on the medial meniscus and medial side of the tibial plateau. Either of these conditions could exist when the knee is in flexion, extension, or in both positions. Either of these conditions, in either or both positions, can damage or accelerate the deterioration of the healthy side of the knee. Moreover, in any case, if too much bone is removed from either side, the prosthesis may be too loose in flexion, extension or in both positions. Accordingly, it is important that the surgeon be able to assess the potential positions of both the condyle to be resected and the condyle to remain native relative to the resected and native proximal tibia, and it is important that the surgeon be able to make this assessment when the knee is in flexion and extension.

SUMMARY OF THE INVENTION

The present invention provides a guide, kit and method which can be used to locate the distal femoral resection plane on one condyle of a femur for receiving a unicompartmental knee prosthesis.

In one aspect, the present invention provides a kit for locating a distal femoral resection plane in uni-compartmental knee surgery. The kit comprises a shim and a combination cutting and spacer guide. The shim includes a shim arm and a mounting member connected to the shim arm. The combination cutting and spacer guide includes a cutting block portion and a guide arm portion. The cutting block portion has an anterior side and a posterior side and surfaces defining a cutting guide slot extending from the anterior side to the posterior side. The cutting guide slot lies in a plane defining the distal femoral resection plane. The cutting block portion further includes a pair of holes extending from the anterior side to the posterior side for mounting the combination cutting and spacer guide to the femur and a shim mounting opening. The guide arm portion has a posterior end spaced from the cutting block portion, a planar femoral surface extending outward from the posterior side of the cutting block portion to the posterior end, and a planar tibial surface extending from the cutting block portion outward to the posterior end. The tibial surface and femoral surface are substantially parallel to and spaced from the distal femoral resection plane. The combination cutting and spacer guide has a shim mounting opening. The shim arm has a planar contact surface for contacting part of the guide arm and a planar contact surface for contacting part of one of the bones of the knee. The mounting member of the shim is sized and shaped to be receivable within the mounting opening of the combination cutting and spacer guide to removably mount the shim to the guide arm.

In another aspect, the present invention provides a combination cutting and spacer guide for use in cutting along a distal femoral resection plane in uni-compartmental knee surgery. The combination cutting and spacer guide includes a cutting block portion and an integral guide arm portion. The cutting block portion has an anterior side and a posterior side and surfaces defining a cutting guide slot extending from the anterior side to the posterior side. The cutting guide slot lies in a plane defining the distal femoral resection plane. The cutting block portion further includes a pair of holes extending from the anterior side to the posterior side for mounting the combination cutting and spacer guide to the femur. The integral guide arm portion has a posterior end, a planar femoral surface, a planar tibial surface, a medial side, a lateral side and a slot. The posterior end is spaced from the cutting block portion. The femoral surface extends from an edge along the posterior side of the cutting block portion to the posterior end. The tibial surface extends from the cutting block portion to the posterior end. The slot is between the femoral surface and the tibial surface and extending from at least one of the medial edge and the lateral edge of the guide arm portion. The tibial surface and femoral surface are substantially parallel to and spaced from the distal femoral resection plane.

In another aspect, the present invention provides a method of resecting the distal end of a single condyle of a femur. The method comprises providing a surgical kit that includes a combination cutting and spacer guide. The combination cutting and spacer guide has a cutting block portion and a guide arm portion. The cutting block portion has an anterior surface, a posterior surface and a cutting guide slot extending from the anterior to the posterior surface. The guide arm portion has a planar femoral surface and a planar tibial surface. The method further comprises resecting a portion of one side of the proximal tibia adjacent one condyle at the distal end of the femur. The guide arm portion of the combination cutting and spacer guide is inserted into the space between the distal end of the femur and resected tibia while the knee is extended. The knee is manipulating with the guide arm portion between the distal end of the femur and resected tibia. The combination cutting and spacer block is temporarily attached to the femur but not to the tibia. A cutting implement is inserted through the cutting slot of the cutting block portion of the combination cutting and spacer block to resect the distal femur along a distal femoral resection plane.

BRIEF DESCRIPTION OF THE DRAWINGS

The invention will be better understood by reference to the figures of the drawings wherein like numbers denote like parts throughout and wherein:

FIG. 23 is a side elevation showing the combination cutting and spacer guide of FIGS. 5-8 shown in position in the gap between the resected proximal tibia and the intact posterior side of one condyle of the femur, with no shims;

FIG. 24 is a side elevation showing the combination cutting and spacer guide of FIGS. 5-8 shown in position in the gap between the resected proximal tibia and the intact posterior side of one condyle of the femur, shown with a femoral shim in place but no tibial shim;

FIG. 25 is a side elevation showing the combination cutting and spacer guide of FIGS. 5-8 shown in position in the gap between the resected proximal tibia and the intact posterior side of one condyle of the femur, shown with a femoral shim and a tibial shim in place;

DETAILED DESCRIPTION

Figure 1:
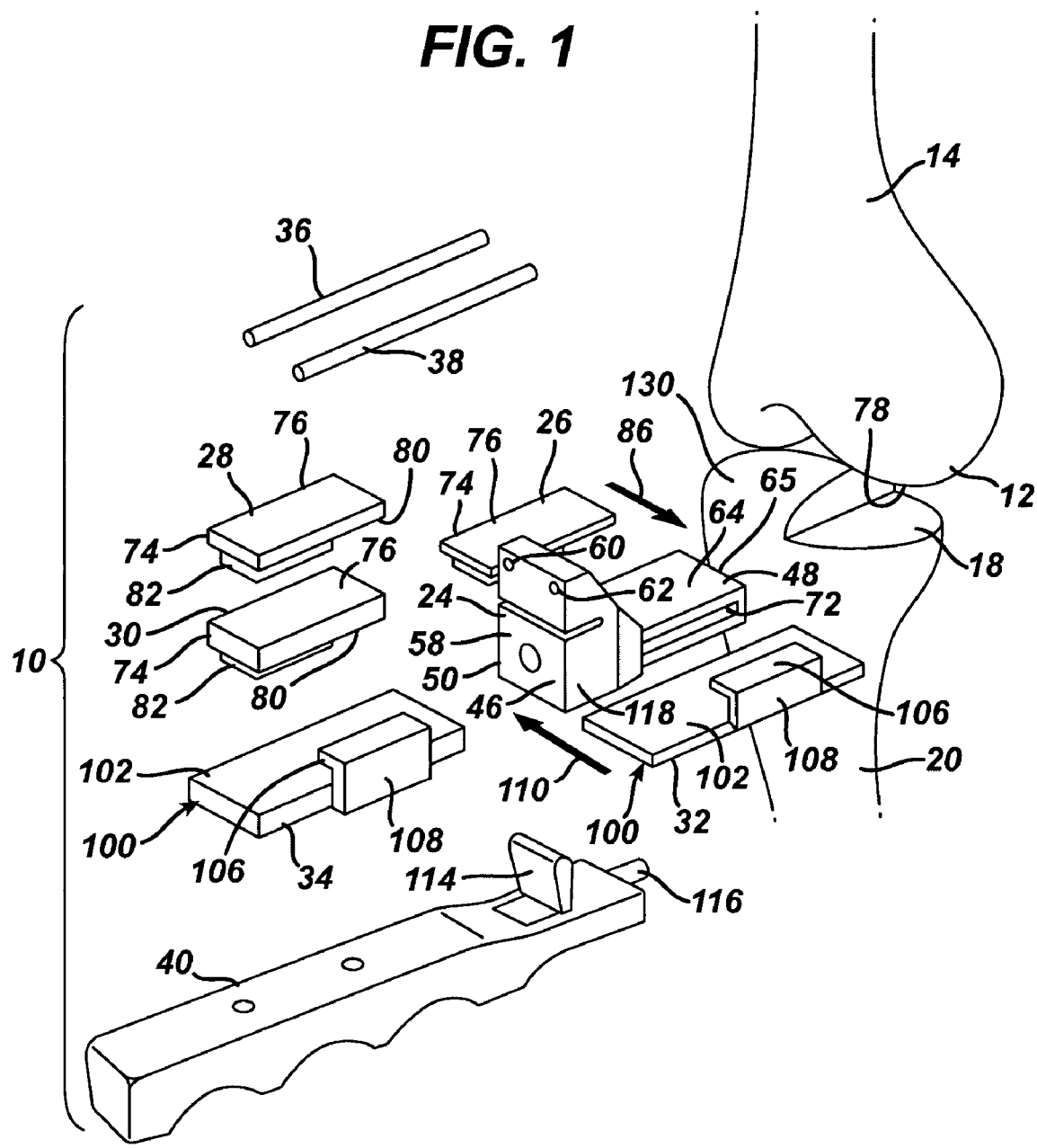
FIG. 1 is perspective view of a first embodiment of a kit embodying the principles of the present invention, shown adjacent to a diagrammatic representation of a knee joint.
Figure 2:
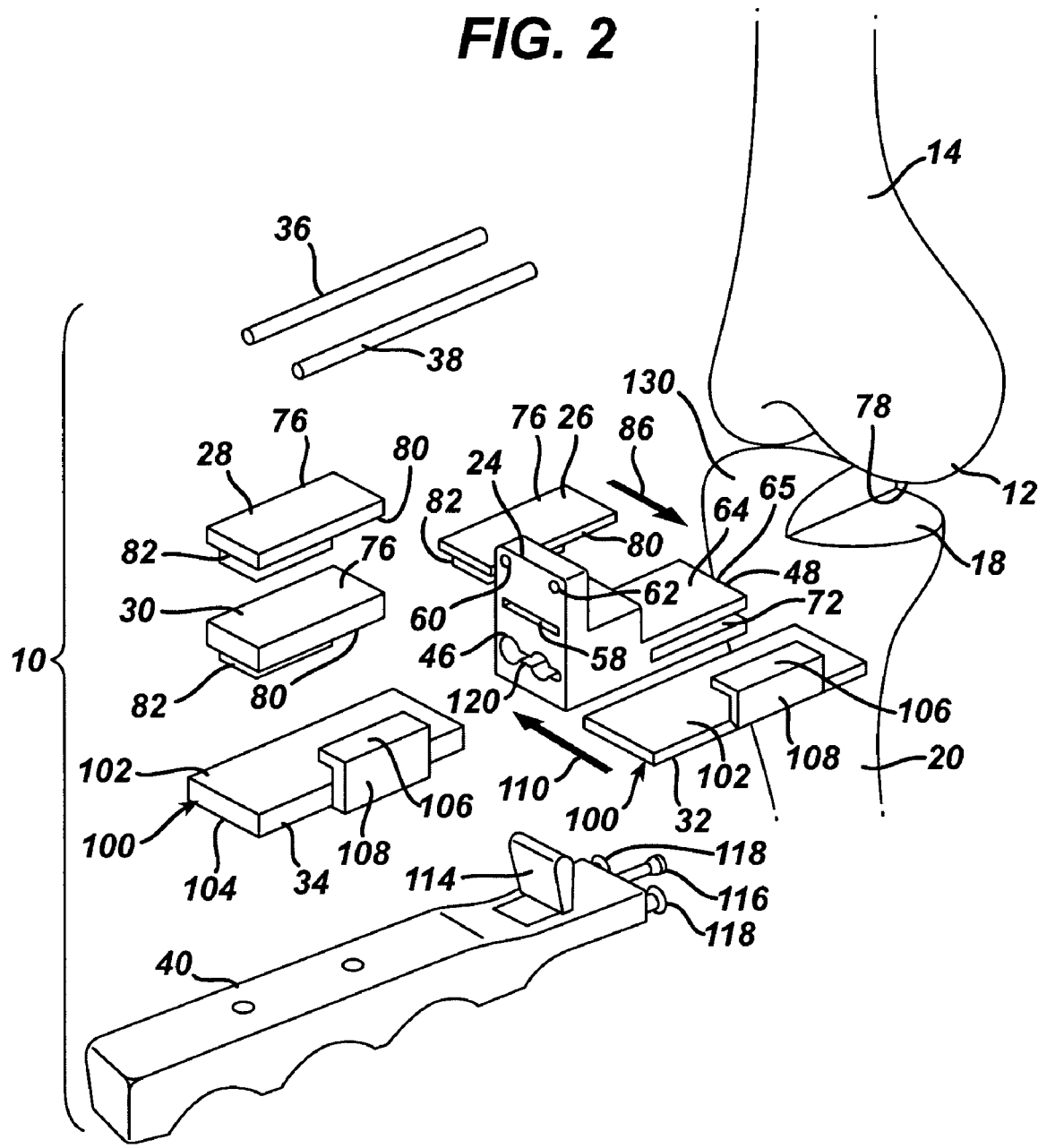
FIG. 2 is a perspective view of a second embodiment of a kit embodying the principles of the present invention, shown adjacent to a diagrammatic representation of a knee joint.
Figure 3:
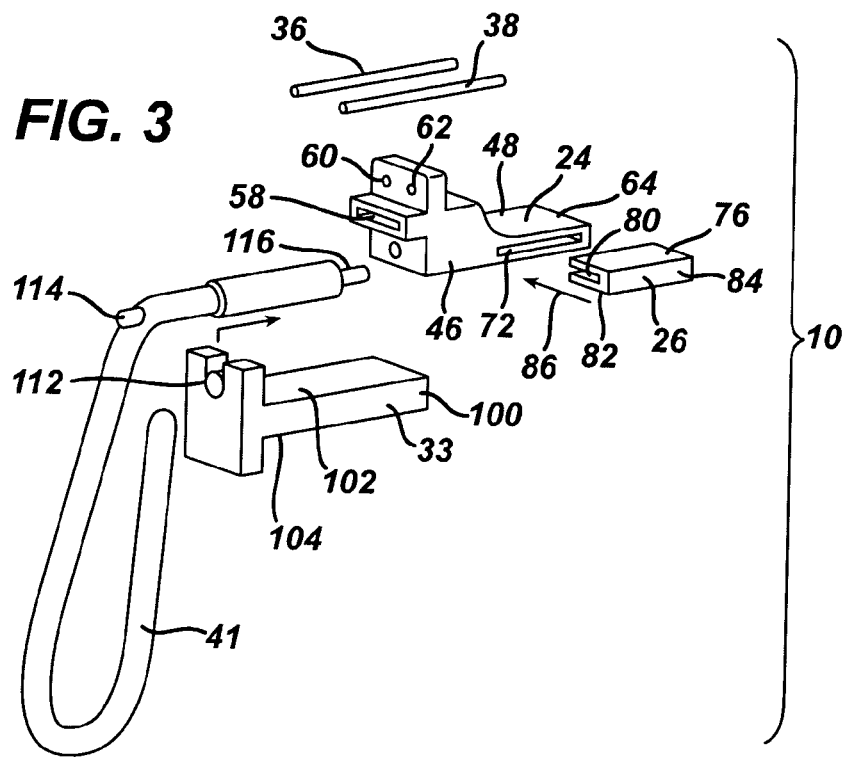
FIG. 3 is a perspective view of a third embodiment of a kit embodying the principles of the present invention.
Figure 4:
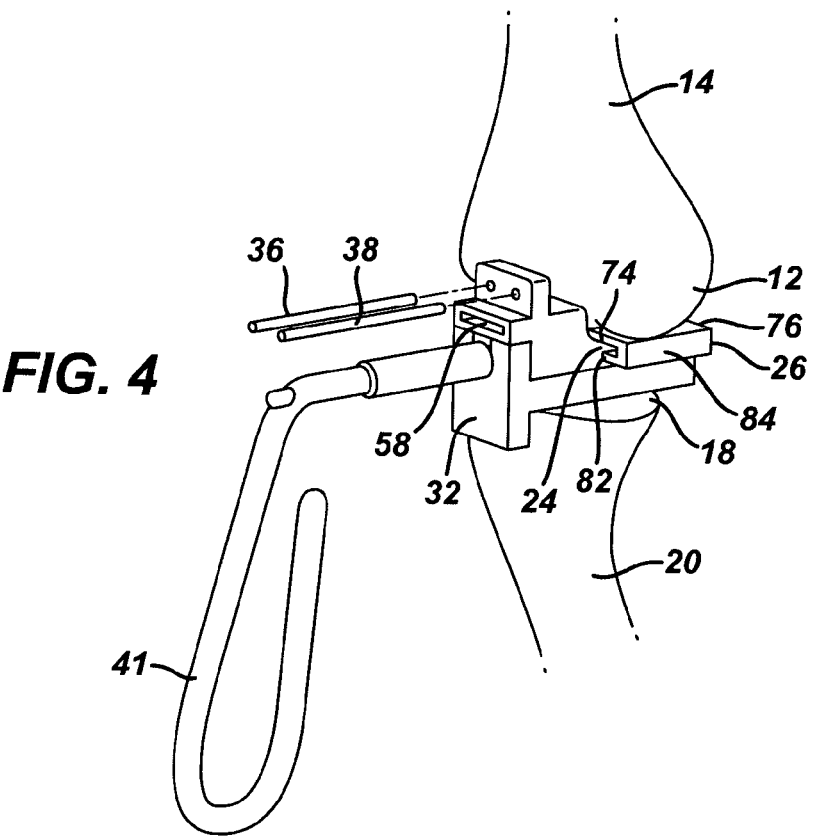
FIG. 4 is a perspective view of the kit of FIG. 3 shown with the combination cutting and spacer guide and shims of the kit in place within the gap of a knee joint, shown diagrammatically.

Three embodiments of the kit and combination cutting and spacer guide of the present invention are illustrated in the accompanying figures, where like reference numbers are used for like parts. In FIGS. 1-3, the three embodiments of the kits are all identified with reference number 10. The kit of the invention is advantageous in unicompartmental knee replacement surgery in that it enables a surgeon to move the patient's leg between extension and flexion, to move the patient's tibia in the medial and lateral directions about the knee while the guide is in place in the gap between the resected tibia and the distal non-resected femur, and to rotate the patient's leg about the anatomic axis of the tibia. Accordingly, the surgeon can evaluate the effect of cutting along the planned distal femoral resection plane while the patient's leg is moved through the natural range of positions. The surgeon can obtain a feel for whether the planned resection will result in undesirable stress on the healthy side of the knee, that is, the side of the knee that will not receive a prosthesis, can evaluate alignment, and can evaluate soft tissue tension and balancing.

Figure 12:
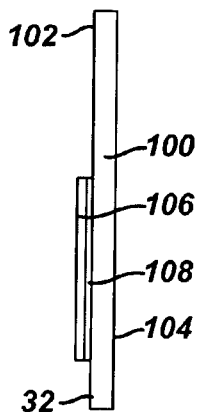
FIG. 12 is a side elevation of the tibial shim of FIG. 9.
Figure 13:
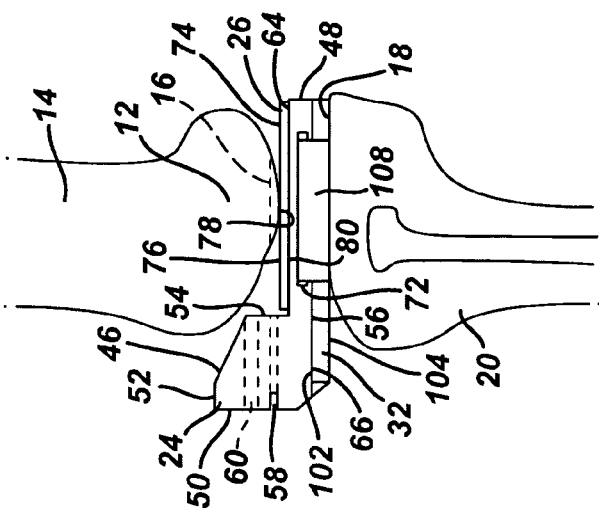
FIG. 13 is a side elevation showing the combination cutting and spacer guide of FIGS. 5-8 shown in position in the gap between the resected proximal tibia and the intact distal end of the femur, with no shims.
Figure 14:
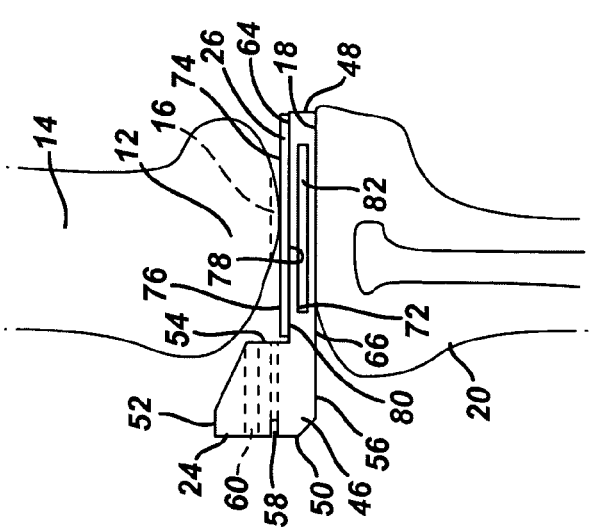
FIG. 14 is a side elevation showing the combination cutting and spacer guide of FIGS. 5-8 shown in position in the gap between the resected proximal tibia and the intact distal end of the femur, shown with a femoral shim in place but no tibial shim.
Figure 15:
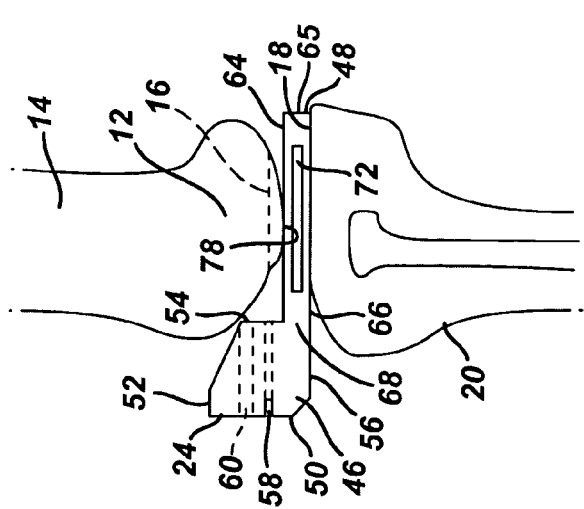
FIG. 15 is a side elevation showing the combination cutting and spacer guide of FIGS. 5-8 shown in position in the gap between the resected proximal tibia and the intact distal end of the femur, shown with a femoral shim and a tibial shim in place.

A first embodiment of a kit 10 for use in determining the location of a distal femoral resection plane for resecting a single condyle 12 of the femur 14 in a knee joint is illustrated in FIG. 1. The distal femoral resection plane, shown at 16 in FIGS. 13-15, is determined relative to a reference surface 18 on a single side of the tibia 20, either the medial side or the lateral side. Determining the position of the distal femoral resection plane 16 allows the surgeon to prepare the femur 14 for implantation of the femoral component of a unicompartmental knee joint prosthesis (not shown in FIGS. 1-22).

The kit 10 may include a combination cutting guide and spacer guide 24, a plurality of femoral shims 26, 28, 30 and a plurality of tibial shims 32, 34. The kits 10 also preferably include anchoring members 36, 38 and a removable handle 40. The kits 10 may include a reciprocating saw 42 or reciprocating saw blade 44 (shown in FIGS. 20 and 22) or other cutting implement as well.

Figure 5:
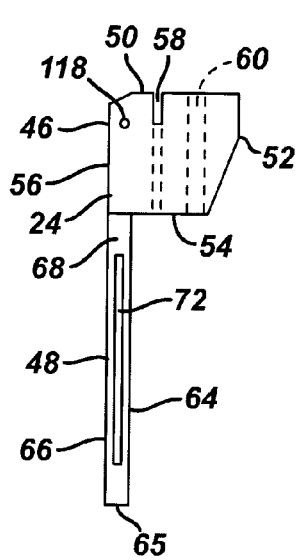
FIG. 5 is a side elevation of the combination cutting and spacer guide of the kit of FIG. 1, shown without any shims attached.
Figure 6:
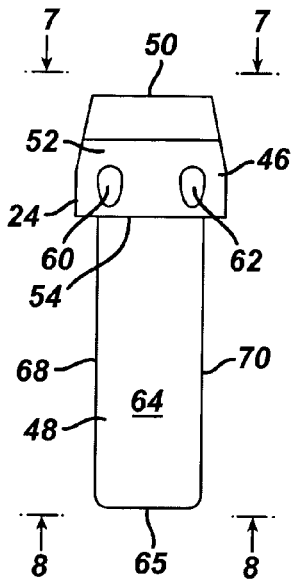
FIG. 6 is a top plan view of the combination cutting and spacer guide of FIG. 5.
Figure 7:
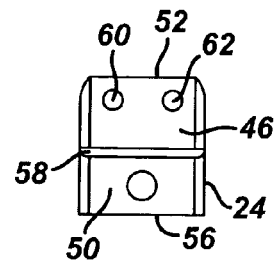
FIG. 7 is an end view of the combination cutting and spacer guide of FIGS. 5-6, taken along line 7-7 of FIG. 6.
Figure 8:
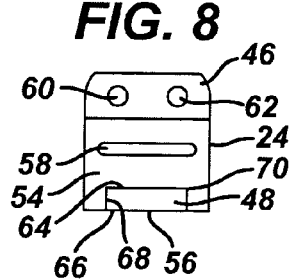
FIG. 8 is an end view of the combination cutting and spacer guide of FIGS. 5-6, taken along line 8-8 of FIG. 6.

Each of the illustrated combination cutting and spacer guide 24 includes a cutting block portion 46 and an integral guide arm portion 48. As shown in FIGS. 5-7, the cutting block portion 46 has an anterior side 50, a proximal side 52, a posterior side 54 and a distal side 56. Spaced interior surfaces in the body of the cutting block portion 46 define a cutting guide slot 58 that extends through the body of the cutting block 46 from the anterior side 50 to the posterior side 54. The cutting block portion 46 also includes a pair of holes 60, 62 extending from the anterior side 50 to the posterior side 54.

As shown in FIGS. 5-7, the integral guide arm 48 extends outward from the posterior side 54 of the cutting guide block 46. The guide arm 48 has a planar femoral surface 64, a planar tibial surface 66, and two sides 68, 70. In the illustrated embodiments, the planar tibial surface 66 of the guide arm 48 is co-planar with the distal side 56 of the cutting block portion 46 of the combination cutting and spacer guide 24. As shown in FIG. 5, the guide arm 48 also has an elongate slot 72 that is generally parallel to and spaced from the guide slot 58 of the cutting block portion 46. The elongate slot 72 is located between the femoral surface 64 and tibial surface 66 of the guide arm 48, and has a height of about 1 mm and a length of about 30 mm in the illustrated embodiment; it should be understood that these dimensions are provided by way of example only and the present invention should not be limited to any particular dimensions unless expressly set forth in the claims. The illustrated elongate slot 72 has medial and lateral openings. In use, the guide arm 48 can be inserted between one condyle 12 of the distal femur 14 and the resected proximal surface 18 of the tibia 20. The combination cutting and spacer guide 24 can be placed with the tibial surface 66 of the guide arm 48 in contact with the reference surface 18 on the tibia 20 and with the femoral surface 64 of the guide arm 48 in contact with the distal end of the femur 14, before the femur is resected, to define a flat distal surface. The femoral surface 64 of the guide arm 48 is spaced between the plane of the cutting guide slot 58 and the plane of the tibial surface 66.

In the embodiments of FIGS. 1 and 3, the guide arm 48 is closed at the posterior end 65, while in the embodiment of FIG. 2, the guide arm 48 is open at the posterior end 65. In the FIG. 2 embodiment, the guide arm 48 essentially comprises two spaced parallel plates joined at the anterior end to the cutting block 46. In the case of the FIG. 2 embodiment, the elongate slot 72 is also accessible from the opening on the posterior side.

Figure 10:
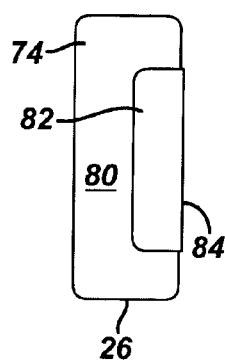
FIG. 10 is a top plan view of one of the femoral shims of the kit of FIG. 1.
Figure 11:
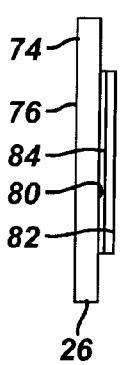
FIG. 11 is a side elevation of the femoral shim of FIG. 10.

Each femoral shim 26, 28, 30 in the embodiments of FIGS. 1-2 is of the same general construction, and it should be understood that the following description applies to all of the femoral shims of the embodiments of FIGS. 1-2. As shown in FIGS. 10-11, the femoral shim 26 comprises an arm 74 having an upper planar contact surface 76 for contacting an intact distal surface 78 of the distal femoral condyle 12 and a lower planar surface 80 for contacting the femoral surface 64 of the guide arm 48. The femoral shim 26 also includes a planar mounting plate 82 and a connecting plate 84. The planar mounting plate 82 is spaced below and parallel to the lower planar contact surface 80 of the arm 74. The planar mounting plate 82 is elongate and sized and shaped to substantially fit within the elongate slot 72 between the femoral and tibial surfaces in one side of the guide arm 48 of the combination guide 24 (see FIG. 14). The connecting plate 84 extends between and connects the planar mounting plate 82 and the arm 74 of the femoral shim 26.

As can be seen from a comparison of the embodiment of FIG. 3, the femoral shims 26 may have larger mounting plates 82 than those illustrated in FIGS. 1-2 and 10-11.

As illustrated in FIGS. 1-2, the kits 10 may include a plurality of femoral shims 26, 28, 30 of different thicknesses, each with a structure as described above. For example, a group of four femoral shims could be provided in sequential thicknesses of 2 mm, 10 mm, 12.5 mm and 15 mm may be provided. It should be understood that these dimensions are provided by way of example only; the invention is not limited to any particular dimension unless expressly called for in the claims.

As shown in FIGS. 1-2, the femoral shims 26, 28, 30 can be mounted on the guide arm 48 of the combination cutting and spacer guide 24 by sliding the femoral shim mounting plate 82 into one of the openings into the elongate slot 72 of the guide arm 48, as shown generally by the arrow labelled 86 in FIGS. 1-3. So mounted, the arm 74 of the femoral shim 26 is positioned above the femoral surface 64 of the guide arm 48, and the top surface 76 of the femoral shim 26 will contact the distal end 78 of the femoral condyle 12, as illustrated in FIGS. 14-15, when the knee is in extension. With the femoral shim 26 in place, the distance between the plane of the cutting slot 58 of the cutting block 46 and the plane of the surface within the gap that contacts the femur is decreased; accordingly, if a femoral shim is in place, less bone will be resected from the distal femur than if the femoral shim were not in place, and damage to the distal condyle can thus be accounted for. This result can be understood from a comparison of the level of the resection line 16 in FIG. 13, where no femoral shim is used, to the resection lines 16 in FIGS. 14 and 15, where femoral shims are in place. The femoral shim 26 can be removed from the guide arm 48 by sliding the femoral shim mounting plate 82 out of the elongate slot 72 of the guide arm 48, in a direction opposite to that of arrow 86 in FIGS. 1-3.

Figure 9:
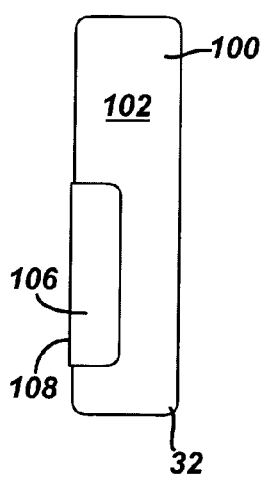
FIG. 9 is a top plan view of one of the tibial shims of the kit of FIG. 1.

Each tibial shim 32, 34 in the embodiments of FIGS. 1-2 is of the same general construction, and it should be understood that the following description applies to all of the tibial shims of the embodiments of FIGS. 1-2. As shown in FIGS. 9 and 12, the tibial shim 32 includes an arm 100 having an upper planar contact surface 102 for contacting the tibial surface 66 of the guide arm 48 and a lower planar contact surface 104 for contacting the resected proximal surface 18 of the tibia 20. The tibial shim 32 also includes a planar mounting plate 106 and a connecting plate 108. The planar mounting plate 106 of the tibial shim 32 is sized and shaped to substantially fit through one of the openings in the guide arm 48 and to fit within the elongate slot 72 between the femoral and tibial surfaces in the lateral side of the guide arm 48. The connecting plate 108 extends between and connects the planar mounting plate 106 and the arm 100 of the tibial shim 32.

The kit may include a plurality of tibial shims 32, 34 of different thicknesses. For example, a group of three tibial shims could be provided in sequential thicknesses of 10 mm, 12.5 mm and 15 mm. The different thicknesses may be provided if, for example, the tibial component of the knee prosthesis is of the modular type that allows for tibial inserts of different thickness, so that the surgeon can evaluate the effects of using different thicknesses of tibial inserts. For example, tibial shims 32, 34 may be provided if the kit is to be useable for both knee prostheses with all polyethylene tibial tray components as well as knee prostheses with mobile bearing tibial components that utilize a metal tibial tray and a polyethylene insert. If the kit is to be used only for prostheses that have a single thickness of tibial component, then it would not be necessary to include tibial shims. It should be understood that the above dimensions are provided by way of example only; the invention is not limited to any particular thickness for the tibial shims unless expressly called for in the claims.

As shown in FIGS. 1-2, the tibial shim 32 can be mounted on the guide arm 48 by sliding the tibial shim mounting plate 106 through one of the openings in the guide arm 48 and into the elongate slot 72 of the guide arm 48 as shown at the arrow marked 110 in FIGS. 1-2. So mounted, the arm of the tibial shim 32 is positioned below and parallel to the planar tibial surface 66 of the guide arm. With the tibial shim in place, the lower surface 104 of the tibial shim 32 will contact the surface 18 of the resected tibia, as shown in FIG. 15. The tibial shim 32 can be removed from the guide arm 48 by sliding the femoral shim mounting plate 106 out of the elongate slot 72 of the guide arm 48 in a direction opposite to that shown at 110 in FIGS. 1-2.

Other designs are possible for the femoral and tibial shims. For example, as shown in FIG. 3, the tibial shim 33 could have an anterior structure, such as that shown at 112 in FIG. 3, that mounts to some part of the handle 41. An additional slot could be formed in the cutting guide block portion 46 below the cutting guide slot 58; femoral shims could be slipped into and out of this additional slot.

Figure 20:
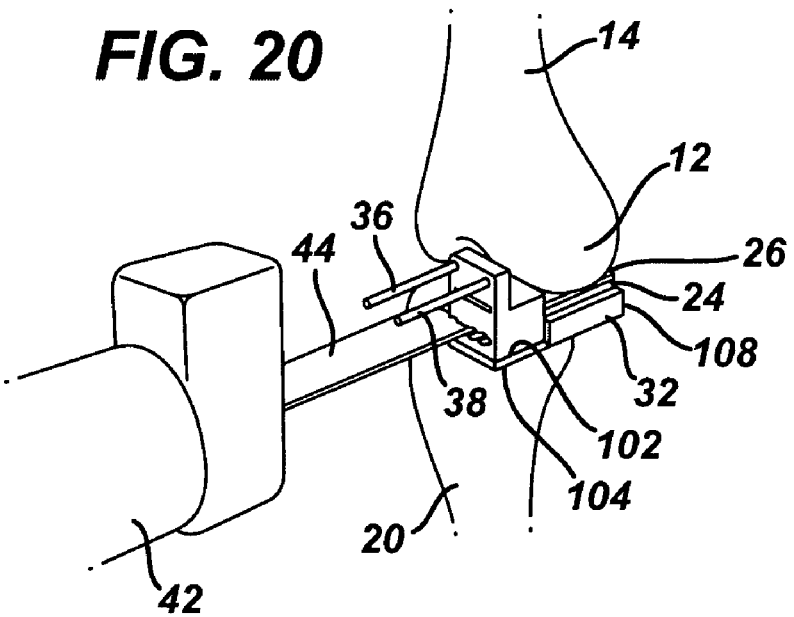
FIG. 20 is a perspective view of a part of the kit of FIG. 2, shown with the handle removed from the assembly of the combination cutting and spacer guide, femoral shim, tibial shim, and anchoring members in position in the gap between the distal end of the femur and the resected proximal tibia, shown with a reciprocating saw to be inserted into the cutting slot of the combination cutting and spacer guide to resect the distal femur, illustrating femoral resection with the ligaments in tension.

It should be understood that although the tibial shims are shown in FIGS. 1, 2 and 20 in conjunction with knees in extension, the tibial shims can also be useful in evaluating the effect of using a particular size or style of tibial element throughout the range of motion of the knee, such as in flexion as shown in FIGS. 23-25.

The combination spacer and cutting block can be used to evaluate the distance between the resected proximal surface of the tibia and the posterior condyle. For example, with the guide arm 48 positioned between the resected proximal surface of the tibia and the posterior condyle 79, as shown in FIGS. 23-25, the surgeon can evaluate the tension that will exist in the joint when the knee is flexed. If the joint is excessively loose in flexion with the combination spacer and cutting guide, the tibial shims can be used to evaluate the potential effect of using different sizes of tibial components or different thicknesses of tibial inserts. The surgeon can then balance the knee in flexion and extension; after determining the size of tibial shim, the surgeon can then use the same size tibial shim with the knee in extension. Moreover, the surgeon may use the evaluation to determine whether soft tissue balancing would be effective without adjusting the size of the tibial implant or insert.

It should be understood that the principles of the present invention can also be applied to other cuts to be made to the femur. For example, a different cutting block could have a slot positioned to make the desired posterior cut to the condyle.

The kits of FIGS. 1-2 also include a plurality of elongate temporary anchoring members 36, 38 to be fixed to the femur through the holes 60, 62 of the cutting block portion 46. The temporary anchoring members can comprise standard devices such as Steinmann pins or drill bits.

For ease in using the combination cutting and spacer guide, a removable tray handle 40, 41 may be included as part of the kit. Removable tray handles 40, 41 are illustrated in FIGS. 1-4, 16-19 and 21. The handle 40, 41 and anterior side 50 of the combination cutting and spacer guide 24 have complementary mechanical mounting structures to allow the handle 40, 41 to be readily attached to and removed from the combination cutting and spacer guide 24. The illustrated removable tray handles 40, 41 include a retractable knob, button or lever 114 operably connected to a central dowel 116; the removable tray handle illustrated in FIG. 2 also includes a pair of spaced stationary dowels with enlarged heads. The anterior side 50 of the combination cutting and spacer guide 24 has a mating receiving opening 120. In the first and third illustrated embodiments (FIGS. 1 and 3), the receiving opening 120 comprises a circular hole; in the second illustrated embodiment (FIG. 2), the receiving opening 120 comprises an elongate slot that includes three spaced enlarged circular areas. In the first embodiment (FIG. 1) retractable pins (not shown) in the dowel 116 are operably connected to the retractable knob or lever 114, and fit within mating passages in the cutting block, such as shown at 118 in FIGS. 1 and 5 to removably secure the handle to the combination guide 24. A similar arrangement is operable with the dowel 116 and button 114 in the third embodiment shown in FIG. 3. In the second embodiment, the central dowel 116 is retractable and is operably connected to the retractable knob or lever 114.

The second illustrated tray handle 40 (FIG. 2) may be attached to the anterior side 50 of the combination cutting and spacer guide 24 in the following manner. The knob or lever 114 of the tray handle 40 is retracted to thereby retract the retractable central dowel 116. The handle 40 is then mounted by inserting the stationary dowels 118 through the two end enlarged circular openings and then indexing the handle to the right, as shown at arrow 124 in FIG. 16, until the stationary dowels 118 are beyond the outside enlarged circular openings. The knob of the handle 114 is then operated as shown at arrow 126 in FIG. 16 to extend the retractable central dowel 116 into the deep opening in the cutting block portion of the combination cutting and spacer guide 24. If desired, the retractable central dowel 116 could be spring biased in either the retracted or extended position. The handle 40 is readily removable by operating the knob to thereby retract the retractable central dowel 116, then indexing the handle 40 to the left until the enlarged heads of the stationary handle dowels 118 can be pulled through the enlarged circular openings of the slot 120.

It should be understood that the above-described mounting mechanisms for the handle are provided by way of example only. The invention is not limited to any particular mounting mechanism unless expressly called for in the claims.

Figure 26:
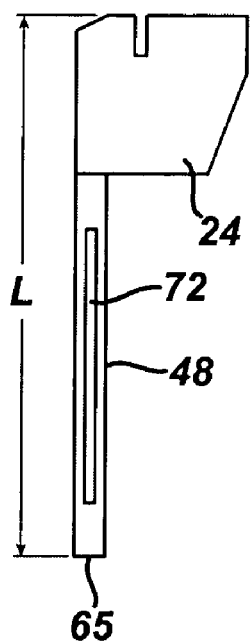
FIG. 26 is a side elevation of a combination cutting and spacer guide.
Figure 27:
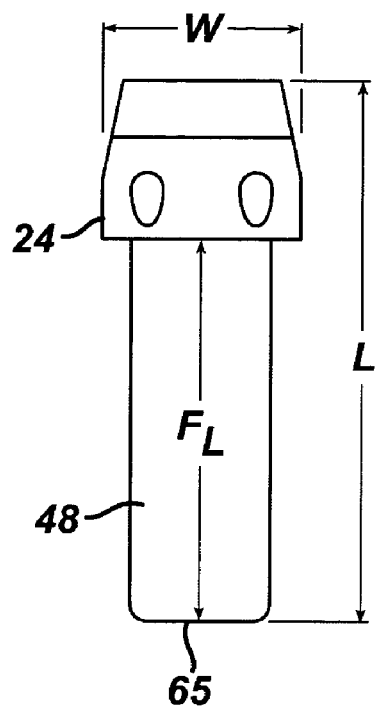
FIG. 27 is a top plan view of the combination cutting and spacer guide of FIG. 26.

Dimensions for various parts of the kits may be as follows. The illustrated combination cutting and spacer guide has an overall length, shown at "L" in FIGS. 26-27, of 67 mm and an overall width, shown at "W" in FIG. 27, of 33 mm. The femoral surface of the guide arm has a length "$F_L$" in FIG. 27 of 47 mm and a width of 17 mm. The tibial surface 66 and distal side 56 of the cutting block portion 46 of the guide arm has a length of 67 mm ("L") and a width of 17 mm. In the illustrated embodiments, the femoral shims 26, 26 have an overall length of about 47 mm and a width of about 17 mm. It should be understood that the above dimensions are provided by way of example only; the invention is not limited to any particular dimension unless expressly called for in the claims.

Figure 28:
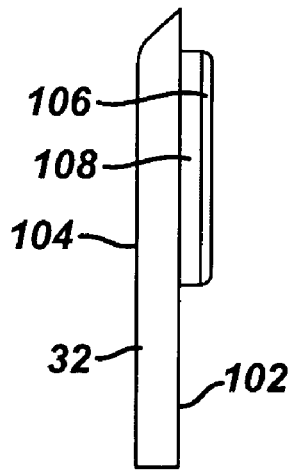
FIG. 28 is a side elevation of a tibial shim that may be used with the combination cutting and spacer guide of FIGS. 26-27.
Figure 29:
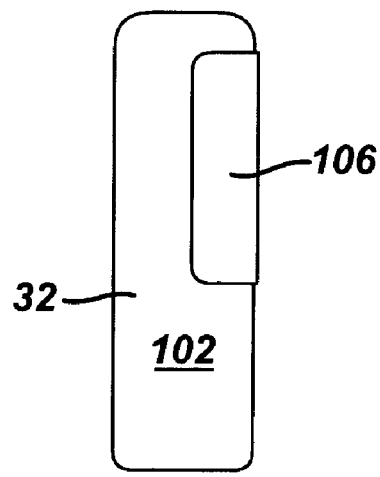
FIG. 29 is a top plan view of the tibial shim of FIG. 28.

In the illustrated embodiments, the tibial shims may have a surface area about the same as that shown for the tibial surface 66 and distal side 56 of the cutting block portion 46 of the combination cutting and spacer guide 24. However, the tibial shims could also be shaped as shown in FIG. 28, with a surface area slightly less than that of the tibial surface 66 and distal side 56 of the combination cutting and spacer guide 24; for example, the surface 102 could have an area of about 60 mm by 17 mm, while the surface 104 could have an area of about 55 mm by 17 mm, with an angled end surface 103 connecting the surfaces 102 and 104. It should be understood that the above dimensions are provided by way of example only; the invention is not limited to any particular dimension unless expressly called for in the claims.

Generally, the surface areas of the tibial surface of the guide arm and the lower tibial surface of the tibial shim should be close to the surface area of the resected surface of the tibial plateau. Generally, the tibial plateaus created through resection of the tibia are about the same size as the tibial component that will be implanted. Tibial bearing components for unicondylar prostheses are commonly provided in different sizes; for example, a small size of a commercially available tibial bearing component for a unicondylar prostheses has a surface area of 683.7 mm$^2$ (1.060 in$^2$), and the large size has a surface area of 1529.3 mm$^2$ (2.370 in$^2$). The smaller size of one example of a unicondylar tibial trial has a maximum overall length (anterior-posterior) of about 41 mm and a maximum overall width (medial-lateral dimension) of about 20 mm. The largest size of the unicondylar tibial trial product has a maximum overall length (anterior-posterior) of about 57 mm and a maximum overall width (medial-lateral dimension) of about 32 mm. With a combination cutting and spacer guide having the above dimensions, the guide arm should extend over the entire anterior-posterior dimension of a small tibial plateau, with about 6 mm of the guide arm extending posteriorly beyond the posterior edge of the resected tibial plateau; the guide arm should extend over at least about 80% of the anterior-posterior dimension of the largest resected tibial plateau. The small amount of potential posterior extension beyond the resected tibial plateau of the smallest tibia should not damage any tissue posterior to the tibia. Although different sizes of combination cutting and spacer guides could be supplied in each kit, each with a different anterior-posterior dimension, it is believed that a single combination cutting and spacer guide of about the above dimensions should be usable for most surgical procedures. With a combination cutting and spacer guide having the above dimensions, the guide arm should extend over about 85% of the largest medial-lateral dimension of the smallest tibial plateau; the guide arm should extend over at least about 53% of the largest medial-lateral dimension of the largest resected tibial plateau. It should be understood that these areas and dimensions are provided by way of example only; the present invention is not limited to any particular dimension or area unless expressly called for in the claims.

Preferably, as shown in FIGS. 18-22, the surface areas of the tibial shim 32 and tibial surface 66 of the guide arm 48 that may contact the resected proximal tibia 18 should be great enough to cover the entire surface area of the resected proximal tibia 18. The surface areas of the femoral shim 26, 28, 30 and femoral surface 64 of the guide arm 48 that may contact one femoral condyle 12 is preferably great enough so that the distal end surface 78 of the femoral condyle 12 bears against the contact surface 64, 76 of the guide arm 48 or shim 26, 28, 30 throughout the entire range of motion that will be tested. Generally, the surfaces 64, 66, 76, 104 of the assembly that contact the tibial plane 18 and end surface 78 of the femoral condyle 12 should be sized and shaped so that the surgeon can manipulate the patient's leg into various positions during surgery with the assembly in place, as described below, and can thereby determine ligament stability and tension with the assembly in place. The shims 26, 28, 30, 32, 34 and guide arm 48 should not be so large as to interfere with this process. Generally, the medial-lateral dimension of the elements of the assembly that may fit between the resected proximal tibial plane 18 and the distal end 78 of the femoral condyle 12 may approximate the medial-lateral dimensions of the tibial tray and uni-condylar femoral component of the uni-compartmental prosthesis that will be implanted. It should be understood that the above areas, shapes and sizes are provided by way of example only; the invention is not limited to any particular area, shape or size unless expressly called for in the claims.

The mounting plates 82, 106 of the shims 26, 28, 30, 32, 34 have thicknesses slightly less than the height of the elongate slot 72. The mounting plates 82, 106 and therefore the tibial and femoral shims 26, 28, 30, 32, 34 can be attached to the guide arm 48 by a friction fit, which secures the pieces together for use during surgery while also allowing for quick and easy disassembly. Each illustrated mounting plate 82, 106 has a width in the medial-lateral direction of less than half the medial-lateral dimension of the guide arm 48, so that the mounting plates 82, 106 for both one tibial shim 32 or 34 and one femoral shim 26, 28, or 30 can be simultaneously received within the elongate slot 72, one shim mounted through the lateral opening and one shim mounted through the medial opening of the slot 72. It should be understood that other mating mounting structures could be used; the invention is not limited to any particular mounting structure unless expressly called for in the claims.

Preferably, the shape of the guide arm 48 is rectangular, with long medial and lateral sides 68, 70. With this shape, elongate openings into the elongate slot 72 can be provided in both the medial and lateral sides 68, 70 of the guide arm 48, so that the guide arm 48 can receive both one tibial shim 32 or 34 and one femoral shim 26, 28 or 30. In addition, if for some reason it was decided to provide a kit with only femoral shims, and no tibial shims, then it would be possible to change the overall shape of the guide arm. For example, in such an instance, the medial side of the guide arm could be made to be straight and the lateral side curved to a shape similar to the shape of the tibial tray component that will eventually be implanted.

The kit 10 and combination cutting and spacer guide 24 of the invention are used to locate the plane 16 for the distal femoral resection while the knee is extended. The surgeon can place the patient's leg in full extension and evaluate axial alignment of the leg. The tension that will be produced from such a femoral resection can be gauged with the patient's leg in full extension as well as in flexion by manipulating the patient's leg with the combination cutting and spacer guide 24 in place in the gap between the distal end 78 of the femoral condyle 12 and the tibial resection plane 18. Since the flexion gap between the femur and tibia should equal the extension gap between the femur and tibia, and since the assembly of the combination cutting and spacer guide 24 and any attached shims 26, 28, 30, 32, 34 fills and defines these gaps, the surgeon can assess the joint with such equal gaps. The surgeon can pivot the lower leg in medial and lateral directions about the knee to gauge the range of motion that will be allowed, and to obtain a feel for the stress that will be produced on the healthy side of the knee joint. The surgeon can also rotate the patient's foot about the anatomical axis of the tibia to evaluate medial ligament stability.

In the surgical procedure for implanting the unicompartmental knee prosthesis, the surgeon may evaluate preoperative radiographs from the anterior-posterior and lateral perspectives with templates to make an initial determination of the proper size of prosthesis. Then, with the knee at about 90° flexion, an incision may be made and the upper tibia is exposed. The proximal tibial resection may be performed using standard instruments and techniques. In addition, a fluoroscopic alignment guide such as that disclosed in U.S. Provisional Patent Application Ser. No. 60/351,782, entitled "Extramedullary Fluoroscopic Alignment Guide", filed by John F. Irving and assigned to DePuy Products, Inc. (the complete disclosure of which is incorporated by reference herein) can be used. Preferably, the proximal tibial resection is performed relative to the mechanical axis of the tibia. Once the proximal tibial resection is complete, a flat resected tibial surface 18 remains, as illustrated in FIGS. 1-2, 4, 13-15 and 17. The healthy side of the proximal tibia, shown at 130 in FIGS. 1-2, remains intact. It should be understood that although the accompanying drawings illustrate the kit 10 in use on the lateral side of the knee, it should be understood that the same kit can be used for medial uni-compartmental knee replacement.

With the cut portion of the proximal tibia removed, the surgeon can size the tibial prosthesis at this stage. In addition, the meniscus and posterior soft tissues may be resected at this point.

Figure 16:
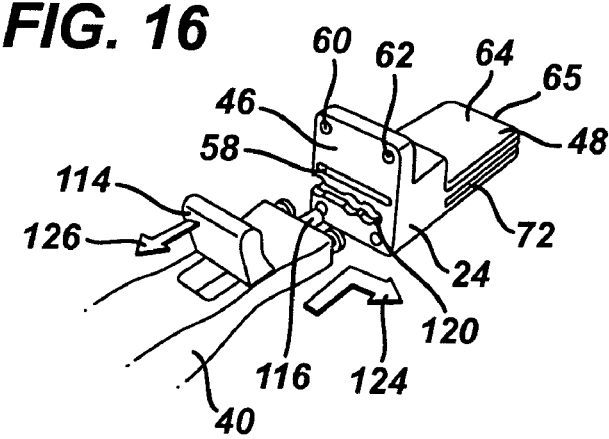
FIG. 16 is a perspective view of the handle and combination cutting and spacer guide of the embodiment of FIG. 2.
Figure 17:
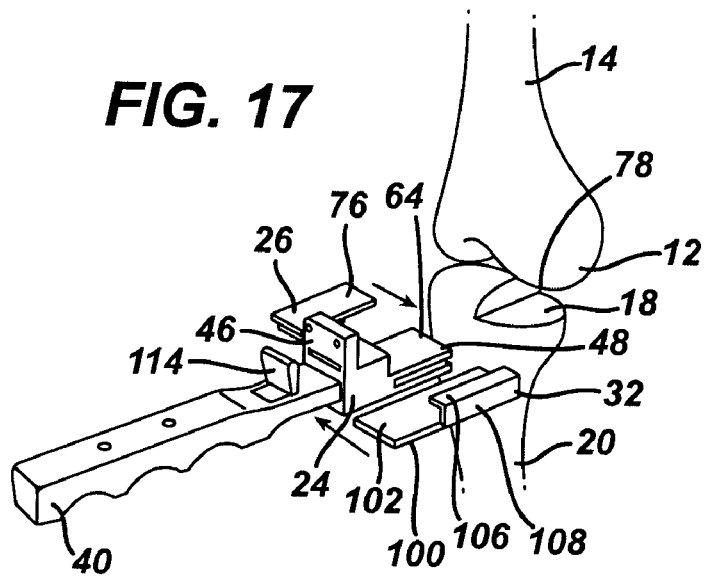
FIG. 17 is a perspective view of the handle connected to the combination cutting and spacer guide of the embodiment of FIG. 2, showing the handle mounted to the combination cutting and spacer guide and showing a femoral shim and tibial shim separate from the assembled handle and combination cutting and spacer guide.

The tray handle 40 is then mounted to the combination guide 24 as shown in FIG. 16, for example. As described above, various mounting mechanisms are possible for use.

With the handle 40 mounted to the combination cutting and spacer guide 24, the guide arm portion 48 can be inserted into the gap between the proximal resected tibial surface plane 18 and the intact distal end 78 of the femoral condyle 12. The tibial surface 66 of the guide arm 48 should be positioned flat against the flat resected tibial surface 18. The surgeon can then determine whether the degree of tension in the soft tissue is proper or whether the degree of tension could be improved. The surgeon can make this evaluation both with the knee in flexion and tension. The surgeon can check axial alignment of the leg with the combination guide in place. The surgeon can also manipulate the patient's lower leg with the combination cutting and spacer guide 24 in position to determine the range of motion available in the medial and lateral directions, may rotate the patient's foot to evaluate medial ligament stability, and to determine if undesirable stress will be created on the intact femur, tibia and meniscus. If the surgeon determines that the gap is insufficient with the leg extended, the surgeon may resect more tibia. If the joint is tight with the leg in flexion, the surgeon may shave the posterior aspect of the femoral condyle, especially if there is no articular cartilage wear on this part of the condyle. Preferably, prior to the initial evaluation, the thinnest femoral shim 26 is assembled onto the combination cutting and spacer guide by sliding the planar mounting plate 82 into the elongate slot 72 in the guide arm 48 until the connecting plate 84 is pressed against the side 68 or 70 of the guide arm 48. So assembled, the planar top and bottom surfaces 76, 80 of the arm 74 of the femoral shim 26 overlie and substantially cover the femoral surface 64 of the guide arm 48 of the combination cutting and spacer guide 24. When this assembly is inserted into the gap between the proximal tibial resection 18 and the intact end 78 of the femoral condyle 12, the top surface 76 of the femoral shim 26 will be nearest the distal end 78 of the femoral condyle 12. This thin shim 26 is used in order to allow for cartilage on the distal femoral condyle 12 that will be lost with the distal resection. The initial evaluation is then performed as described above with this thin femoral shim 26 in place.

If the surgeon determines from the initial evaluation that there is inadequate tension in the soft tissue with the thinnest femoral shim 26, the surgeon may remove the combination cutting and spacer guide assembly 24, 26 and 40 (that is, the assembly including the handle, the combination cutting and spacer guide and femoral shim) from the gap between the tibial resection 18 and the intact distal end 78 of the femoral condyle 12. The surgeon may remove the thinnest femoral shim 26 and replace it with another femoral shim 28 of greater thickness, place the new assembly 24, 28, 40 into the gap between the tibial resection plane 18 and the intact distal end 78 of the femoral condyle 12 and evaluate the tension while moving the patient's leg as described above. The surgeon may continue this process using femoral shims 30 in sequential thicknesses until the surgeon is satisfied that the tension is adequate, but not excessive.

FIG. 13 illustrates a knee joint with the combination cutting and spacer guide 24 in place, with no femoral shim and no tibial shim. FIG. 14 illustrates a knee joint with the combination cutting and spacer guide 24 in place, with a femoral shim 26 and no tibial shim. FIG. 15 illustrates a knee joint with the combination cutting and spacer guide 24 in place, with both a femoral shim 26 and tibial shim 32. As can be seen from a comparison of FIGS. 13 and 14-15, the addition of the femoral shim 26 lowers the level of femoral resection; in effect, less bone will be removed from the distal end 78 of the femoral condyle 12 than in the case of the femoral resection plane illustrated in FIG. 13.

Figure 18:
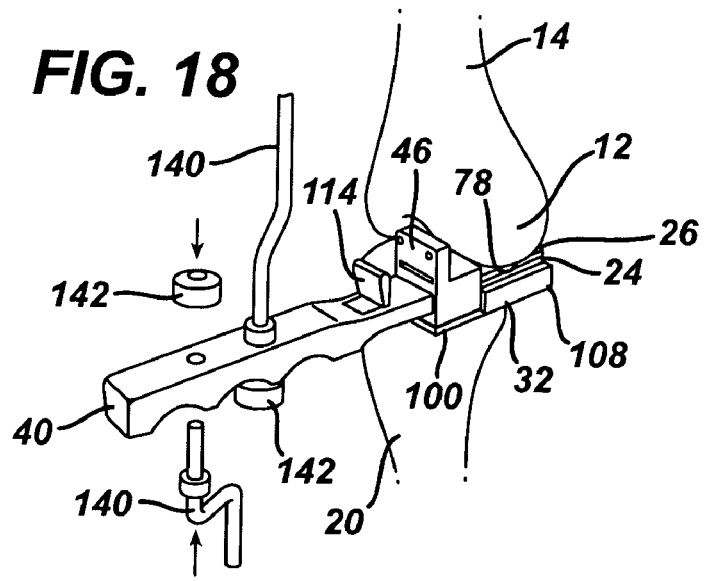
FIG. 18 is a perspective view of a part of the kit of FIG. 2, shown with the assembly of the handle, combination cutting and spacer guide, femoral shim and tibial shim in position in the gap between the distal end of the femur and the resected proximal tibia, shown with part of an external alignment guide attached to the handle and with part of the external alignment guide shown removed from the handle.

As shown in FIG. 18, if desired, the handle 40 can include holes to receive alignment rods 140 and complementary connecting devices 142, such as by providing a threaded end on the alignment rod 140 and a threaded nut 142 to mount the alignment rod 140 to the handle 40. Before performing the resection, the surgeon can check the patient's mechanical axis against the alignment that will result with the implant in place. The range of angular motion that will be available with the unicompartmental implant may also be more easily visualized by manipulating the patient's leg with the alignment rod 140 or alignment rods in place. Notably, the presence of the alignment rod 140 does not interfere with the surgeon's manipulation of the patient's leg during the evaluation. No intramedullary rod is used in this procedure.

Throughout the entire evaluation process, that is, through the entire range of motion of the patient's leg as described above, the combination guide 24 is in contact with substantially the entire surface area of the resected portion 18 of the proximal tibia. If a tibial shim 32, 34 is used, then the lower surface 104 of the tibial shim 32, 34 is in contact with substantially the entire surface area of the resected portion 18 of the proximal tibia throughout the entire evaluation process. If no tibial shim is used, then the tibial surface 66 of the arm 48 of the combination guide 24 is in contact with substantially the entire surface area of the resected portion 18 of the proximal tibia throughout the entire evaluation process. In addition, throughout the entire evaluation process, part of one intact distal femoral condyle 12 is in contact with the combination guide 24. If a femoral shim 26, 28, 30 is used, then the upper surface 76 of the femoral shim contacts part of one intact distal femoral condyle throughout the entire evaluation process. If no femoral shim is used, then the femoral surface 64 of the combination guide 24 contacts part of one intact distal femoral condyle throughout the entire evaluation process.

As can be understood from an analysis of FIGS. 13-15, the thickness of the guide arm 48 of the combination guide 24 and any shim 26, 28, 30, 32, 34 mounted on the guide arm 48 should place the intact distal femur 78 in the position it would have been in a natural, healthy state. Essentially, the sum of the thicknesses of the guide arm 48 the combination guide 24 and any shims 28, 32 mounted on the guide arm 48 should equal the sum of the thickness of the bone resected from the proximal tibia (the distance between 18 and 78 in FIGS. 13-15) and the amount of articular cartilage lost to disease at the distal femur. In the illustrated embodiments, the thickness of the guide arm 48, or sum of the thicknesses of the guide arm 48 and tibial shims 32 or 34, equals the thickness of bone resected from the proximal tibia. Thus, in the illustrated embodiments, the thickness of the femoral shim 26, 28 or 30 used generally equates with the amount of articular cartilage that has been lost from the femoral condyle most typically as a result of osteoarthritis.

Figure 19:
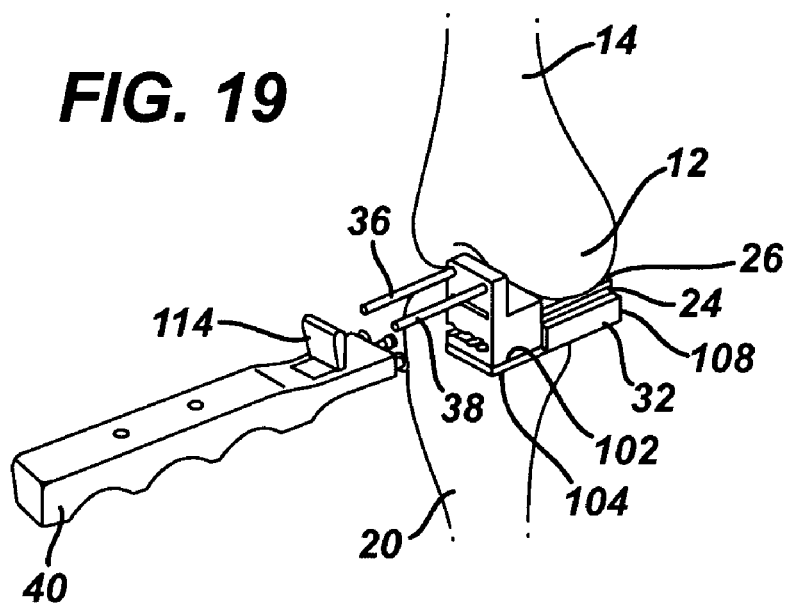
FIG. 19 is a perspective view of a part of the kit of FIG. 2, shown with the handle removed from the assembly of the combination cutting and spacer guide and the femoral shim and tibial shim, shown with the assembly of the combination cutting and spacer guide, femoral shim and tibial shim in position in the gap between the distal end of the femur and the resected proximal tibia, and shown with the anchoring members of the kit in place securing the assembly to the distal femur, illustrating femoral resection with the ligaments in tension.
Figure 21:
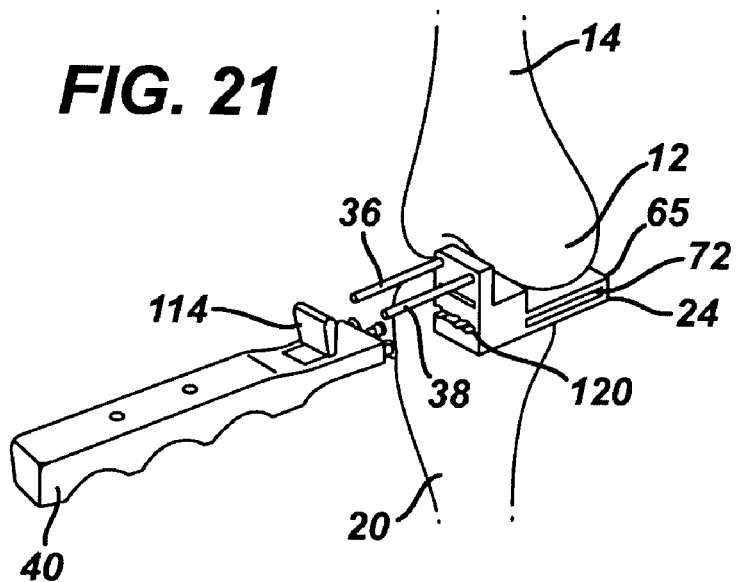
FIG. 21 is a perspective view of a part of the kit of FIG. 2, shown with the handle and shims removed from the assembly of the combination cutting and spacer guide and anchoring members, shown with the combination cutting and spacer guide in position in the gap between the distal end of the femur and the resected proximal tibia, and shown with the anchoring members of the kit in place securing the combination to the distal femur after the shims have been removed, illustrating femoral resection with the ligaments relaxed.
Figure 22:
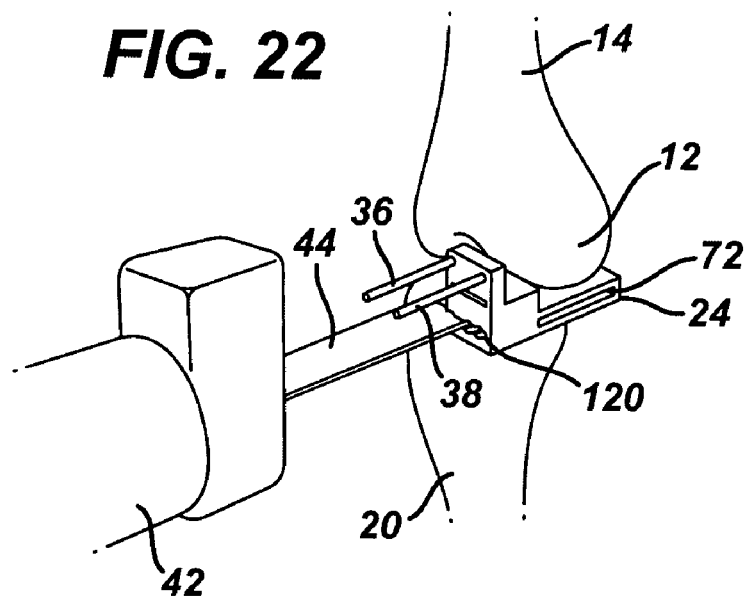
FIG. 22 is a perspective view of a part of the kit of FIG. 2, shown with the handle and shims removed from the assembly of the combination cutting and spacer guide and anchoring members, shown with the combination cutting and spacer guide in position in the gap between the distal end of the femur and the resected proximal tibia, shown with a reciprocating saw to be inserted into the cutting slot of the combination cutting and spacer guide to resect the distal femur, illustrating femoral resection with the ligaments relaxed.

Once the surgeon is satisfied with the alignment of the leg, stability of the knee and degree of tension in the soft tissue of the knee, the surgeon may insert the anchoring members 36, 38 through the holes 60, 62 in the cutting block portion 46 of the combination cutting and spacer guide 24. The combination cutting and spacer guide 24 may thus be pinned in place on the distal femur as shown in FIGS. 4 and 19-22. The surgeon has the option of performing the distal femoral resection with the ligaments in tension as shown in FIGS. 19-20 or with the ligaments relaxed as shown in FIGS. 21-22.

To perform the resection with the ligaments in tension or relaxed, the surgeon removes the tibial tray handle 40 from the cutting block portion by retracting the knob or lever 114 to retract the retractable element. The manner in which the handle is removed will depend on the type of mechanical connection used, as discussed above. The combination guide 24, anchoring pins 36, 38 and any shims remain in place, as shown in FIGS. 19 and 21.

To perform the resection with the ligaments relaxed, the surgeon slips the combination guide 24 with any shims off of the pins 36, 38 or drill bits, and the femoral shim 26 is removed from the combination cutting and spacer guide 24. If a tibial shim is used, it may also be removed at this time. The combination cutting and spacer guide 24 is then replaced on the pins 36, 38 or drill bits. The surgeon then inserts the blade 44 of a reciprocating saw 42 through the cutting slot 58 to make the distal femoral resection along the plane 16, as shown in FIGS. 20 and 22. The combination cutting and spacer guide 24 and the pins 36, 38 or drill bits may then be removed. The surgeon may then perform other resections of the anterior and posterior femoral condyle and can make chamfer cuts.

The kit may include a special-sized surgical saw blade 44. The blade 44 may be more narrow than standard surgical saw blades to fit within the cutting guide slot of the combination guide. Since the narrower saw blade may not cut through the entire femur, the surgeon may make an initial cut with the narrow saw blade through the cutting guide slot, remove the combination guide and anchoring members, and then complete the distal femoral cut. In completing the distal femoral cut, the knee may be placed in flexion if there is concern about posterior capsule damage.

The surgeon then removes the resected portion of the distal femur and completes posterior soft tissue clearance.

Notably, throughout the entire process described above, there is no use of any intramedullary rod. In addition, although an extramedullary alignment rod 140 could be attached to the tray handle 40 if desired to check alignment with the patient's mechanical axis, it is not necessary to do so.

Once the distal femoral cut has been completed, the surgeon inserts a femoral sizing and drill guide (not illustrated in FIGS. 1-22). The size of the guide is determined initially from templating the lateral radiograph. The size is chosen to closely reach the anterior limit of the distal femoral cut. The sizing and drill guide is positioned to best fit the distal femoral surface, and tapped into the bone. Two holes are drilled through the guide. Pins on the femoral chamfer guide (not shown in FIGS. 1-22) are inserted into the two drilled holes. The femoral chamfer guide is tapped gently into place with a small hammer. The patella is pulled laterally for the side pine knob on the femoral chamfer guide to miss the patella. The femoral chamfer guide is stabilized by drilling a side pin into the bone through a hole in the femoral chamfer guide. With the femoral chamfer guide in place, the surgeon can then perform three chamfer cuts. After completing the chamfer cuts, the guide is removed and the posterior cuts are completed. The posterior chamfer bone is removed, but the anterior chamfer bone is left in place. A femoral peg drill guide (not shown in FIGS. 1-22) is inserted and the posterior and anterior peg holes are drilled. The femoral peg drill guide is removed, and a portion of anterior bone that had been cut by the femoral peg drill guide is removed.

Next, the surgeon may size the tibia from the resected tibial plateau bone and then the tibial lug guide (not shown in FIGS. 1-22) is trialed for maximum tibial plateau coverage. The tibial lug guide that best covers the tibial plateau is inserted, and an anterior punch (not shown in FIGS. 1-22) is tapped in to make the anterior lug hole. With the anterior punch in place, a posterior punch (not shown in FIGS. 1-22) is inserted and then tapped in.

The femoral trial prosthesis (not shown in FIGS. 1-22) is inserted with the knee flexed. A tibial trial (not shown in FIGS. 1-22) is selected and mounted on an inserter. The tibial trial is inserted with the knee in extension. The inserter is removed and the knee is assessed in flexion.

If the surgeon is satisfied after performing the trial, the tibial prosthesis (not shown in FIGS. 1-22) may be trial fit to ensure the pegs can be inserted. The tibial prosthesis is then cemented in place. After the tibial cement has cured, the prosthetic femoral component (not shown in FIGS. 1-22) is trial fit. If the surgeon is satisfied, the prosthetic femoral component is cemented in place. After the cement has cured, the surgeon can check flexion and extension and then close the wound, bandage the leg, and review anterior-posterior and lateral radiographs to confirm the positions of the prosthetic components.

It should be understood that the above-described surgical procedure is provided as an example only. The invention is not limited to any particular acts or steps unless expressly set forth in one of the claims.

The combination cutting and spacer guide 24, shims 26, 28, 30, 32, 34, handle 40, 41, anchoring devices 36, 38 and alignment rods 140 (if provided) will generally be made from a metal, such as is commonly used in the manufacture of surgical instruments. Stainless steel, for example, may be used for all the components of the kit 10. If desired, portions of the kit 10 can be made of polymers that are suitable for sterilization. However, if a polymer is to be used, it is preferred that the polymer be used for parts such as the shims 26, 28, 30, 32, 34 that do not receive or bear against any part of the cutting device. The holes 36, 38, 118 and slots 58, 72, 120 may be machined in place. The anchoring devices 36, 38 may comprise standard Steinmann pins or drill bits or other standard devices.

While only specific embodiments of the invention have been described and shown, it is apparent that various alternatives and modifications can be made thereto. Those skilled in the art will also recognize that certain additions can be made to the illustrative embodiments. It is, therefore, the intention in the appended claims to cover all such alternatives, modifications and additions as may fall within the true scope of the invention.

We claim:

1. A kit for locating a distal femoral resection plane in uni-compartmental knee surgery, the kit comprising:
 a first shim including a first shim arm and a mounting member connected to the first shim arm;
 a second shim including a second shim arm and a mounting member connected to the second shim arm; and
 a combination cutting and spacer guide including a cutting block portion and a guide arm portion,
  the cutting block portion having an anterior side and a posterior side and surfaces defining a cutting guide slot extending from the anterior side to the posterior side, the cutting guide slot lying in a plane defining the distal femoral resection plane,
  the guide arm portion having a posterior end spaced from the cutting block portion, a planar femoral surface extending outward from the posterior side of the cutting block portion to the posterior end, and a planar tibial surface extending from the cutting block portion outward to the posterior end, the planar femoral surface lying in a plane spaced from the plane of the planar tibial surface, the planes of the tibial surface and femoral surface being substantially parallel to and spaced from the distal femoral resection plane of the cutting guide slot;
 the combination cutting and spacer guide having a shim mounting opening;
 wherein each shim arm has a planar guide arm contact surface for contacting part of the guide arm portion and a planar bone contact surface for contacting part of one of the bones of the knee, the mounting member being sized and shaped to be receivable within the mounting opening of the combination cutting and spacer guide to removably mount the shim to the guide arm portion;
 wherein the planar bone contact surface of each shim arm is parallel to the cutting guide slot when the shim is mounted to the guide arm portion;
 wherein the planar guide arm contact surface of at least one of the shim arms has a surface area substantially the same as the surface area of the femoral surface of the guide arm portion of the combination cutting and spaced guide;
 wherein the planar guide arm contact surface of at least one of the shim arms covers at least a portion of one of the planar femoral surface and the planar tibial surface of the guide arm portion when the shim is mounted to the guide arm portion;
 wherein the first and second shims are discrete components separately mountable to the guide arm portion;
 wherein each shim arm has a thickness between the guide arm contact surface and the bone contact surface; and
 wherein the thickness of the first shim arm is less than the thickness of the second shim arm.

2. A kit for locating a distal femoral resection plane in uni-compartmental knee surgery, the kit comprising:
   a femoral shim including a shim arm and a mounting member connected to the shim arm; and
   a combination cutting and spacer guide including a cutting block portion and a guide arm portion,
      the cutting block portion having an anterior side and a posterior side and surfaces defining a cutting guide slot extending from the anterior side to the posterior side, the cutting guide slot lying in a plane defining the distal femoral resection plane,
      the guide arm portion having a posterior end spaced from the cutting block portion, a planar femoral surface extending outward from the posterior side of the cutting block portion to the posterior end, and a planar tibial surface extending from the cutting block portion outward to the posterior end, the tibial surface and femoral surface being substantially parallel to and spaced from the distal femoral resection plane;
   the combination cutting and spacer guide having a shim mounting opening;
   wherein the femoral shim arm has a planar contact surface for contacting part of the guide arm and a planar contact surface for contacting part of femur and has a surface area substantially the same as the surface area of the femoral surface of the guide arm of the combination cutting and spacer guide;
   wherein the mounting member of the femoral shim is sized and shaped to be receivable within the mounting opening of the combination cutting and spacer guide to removably mount the femoral shim to the guide arm;
   the kit further comprising at least one tibial shim having a tibial shim arm and a tibial shim mounting member connected to the tibial shim arm wherein the tibial shim arm has a planar contact surface for contacting part of the guide arm and a planar contact surface for contacting part of the tibia, the tibial shim mounting member being sized and shaped to be receivable within the shim mounting opening of the combination cutting and spacer guide to removably mount the tibial shim to the guide arm, the tibial shim and the femoral shim being discrete elements separately mountable to the combination cutting and spacer guide.

3. The kit of claim 2 wherein the planar contact surface of the tibial shim arm has a larger surface area than the surface area of the femoral shim.

4. The kit of claim 1 wherein the cutting block portion is removably mountable to the femur.

5. The kit of claim 4 wherein the cutting block portion includes a plurality of holes extending from the anterior side to the posterior side for mounting the combination cutting and spacer guide to the femur, the kit further comprising anchoring members receivable within the holes in the cutting block portion and a cutting member receivable within the cutting guide slot.

6. The kit of claim 1 wherein the guide arm portion comprises a pair of spaced parallel plates integral with the cutting block portion.

7. The kit of claim 1 wherein the cutting block portion and the guide arm portion are integral.

8. The kit of claim 7 wherein the cutting block portion has a bottom surface co-planar with the tibial surface of the guide arm portion.

9. The kit of claim 1 wherein the guide arm portion and first shim are sized to be received on a single side of the tibia.

10. The kit of claim 1 wherein the tibial surface of the guide arm portion has a maximum medial-lateral dimension of 32 mm and a maximum anterior-posterior dimension of 57 mm.

11. The kit of claim 1 wherein the combination cutting and spacer guide has a maximum anterior-posterior dimension along the tibial surface of 67 mm.

12. The kit of claim 1 wherein the femoral surface of the guide arm portion has a maximum medial-lateral dimension of 17 mm and a maximum anterior-posterior dimension of 47 mm.

13. The kit of claim 1 wherein the shim mounting opening of the combination cutting and spacer guide comprises an elongate slot extending from the medial to the lateral side of the guide arm portion.

14. The kit of claim 13 wherein the mounting member of each shim comprises a planar member parallel to and overlying a portion of one of the surfaces of the shim arm.

15. The kit of claim 14 wherein the mounting member of each shim is sized and shaped so that the mounting members of the first and second shims can be received simultaneously in the elongate slot.

* * * * *